(12) United States Patent
Matsumoto et al.

(10) Patent No.: US 7,518,111 B1
(45) Date of Patent: Apr. 14, 2009

(54) MAGNETIC ELECTRON MICROSCOPE

(75) Inventors: Takao Matsumoto, Moroyama (JP);
Masanari Koguchi, Kunitachi (JP)

(73) Assignee: Hitachi, Ltd., Tokyo (JP)

( * ) Notice: Subject to any disclaimer, the term of this patent is extended or adjusted under 35 U.S.C. 154(b) by 376 days.

(21) Appl. No.: 11/543,787

(22) Filed: Oct. 6, 2006

(30) Foreign Application Priority Data

Oct. 7, 2005 (JP) ............................. 2005-294276

(51) Int. Cl.
*H01J 37/27* (2006.01)
*G01N 23/04* (2006.01)

(52) U.S. Cl. ...................................................... 250/311
(58) Field of Classification Search .................. 250/311
See application file for complete search history.

(56) References Cited

U.S. PATENT DOCUMENTS 5,814,815 A * 9/1998 Matsumoto et al. ......... 250/311
6,590,209 B1 * 7/2003 Bajt ........................... 250/307

FOREIGN PATENT DOCUMENTS

JP 2002-117800 4/2002

OTHER PUBLICATIONS

J. Cumings, et al., "Carbon Nanotube Electrostatic Biprism: Principle of Operation and Proof of Concept", Microsc. Micoanal. 10, 420-424, 2004.
M. Teague, "Deterministic Phase Retrieval: a Green's Function Solution", Optical Society of America., vol. 73, No. 11, Nov. 1983.
V.V. Volkov, et al, "Lorentz Phase Microscopy of Magnetic Materials", Ultramicroscopy 98 (2004) 271-281.

* cited by examiner

*Primary Examiner*—Jack I Berman
(74) *Attorney, Agent, or Firm*—Mattingly, Stanger, Malur & Brundidge, P.C.

(57) ABSTRACT

Below 50-nm-diameter extremely narrow electrically-conductive fiber is used instead of the electron beam biprism used in the conventional interference electron microscope method. A phenomenon is utilized where a focus-shifted shadow of this fiber is shifted from a straight line by a distance which is proportional to a differentiation of phase change amount of an electron beam due to a sample with respect to a direction perpendicular to the fiber. The phase change amount is quantified by calibrating this shift amount through its comparison with a shift amount caused by another sample in terms of which the corresponding phase change amount has been quantitatively evaluated in advance. The differentiation amount of the quantified phase change in the electron beam due to the sample is visualized, or eventually, is integrated thereby being transformed into absolute phase change amount to be visualized.

6 Claims, 8 Drawing Sheets

MAGNETIC ELECTRON MICROSCOPE

INCORPORATION BY REFERENCE

The present application claims priority from Japanese application JP 2005-294276 filed on Oct. 7, 2005, the content of which is hereby incorporated by reference into this application.

BACKGROUND OF THE INVENTION

1. Field of the Invention

The present invention relates to electron beam apparatuses such as an electron microscope for allowing the phase change distribution of an electron beam due to the magnetic-field structure of a sample to be quantitatively visualized with a high resolution by taking advantage of the electron beam.

2. Description of the Related Art

In recent years, high-performance implementation of magnetic materials has been under way at a tremendous rate. As a result, measurement techniques for visualizing the magnetic-domain structures at nanometer level have become absolutely necessary for the development of new raw materials. Of these measurement techniques, a methodology which allows implementation of the highest spatial resolution and quantitative evaluation is the interference electron microscope method such as the off-axis electron beam holography method.

Hereinafter, referring to FIG. 2, the explanation will be given below-concerning the principle of the off-axis electron beam holography method. An electron beam, which is extracted from an electron source 1 by applying a voltage to a first extraction electrode 2 and a second extraction electrode 3, is accelerated up to a predetermined velocity by an acceleration electrode 4. Moreover, an electron beam with a high parallelism is formed by using such components as a first condenser lens 5 and a second condenser lens 6, and then a sample 7 is irradiated with the high-parallelism electron beam. Next, a voltage is applied to an electron beam biprism 19 which is located between an objective lens 8 and an image-forming lens system 11. As a result of this voltage application, an electron beam which has passed through the sample 7 and an electron beam which has passed through the vacuum in the vicinity of the sample 7 are superposed on each other on an image surface of the objective lens 8. This superposition forms an interference fringe, i.e., a hologram 10. Furthermore, this hologram 10 is magnified by the image-forming lens system 11, and is image-formed on a fluorescent plate 13, then being inputted into a detector 14. An input image from the detector 14 is introduced into a CPU 16 via an A/D converter 15. Then, after being subjected to an appropriate image processing, the input image is outputted to a display apparatus 18. Here, operation conditions on the components, such as the electron source 1, the first extraction electrode 2, the second extraction electrode 3, the acceleration electrode 4, the first condenser lens 5, the second condenser lens 6, the objective lens 8, the electron beam biprism 19, and the image-forming lens system 11, are controlled from the CPU 16 via a D/A converter 17. This interference fringe, essentially, is a one which should become straight lines. However, this interference fringe is phase-modulated by a magnetic field inside or outside the sample 7, thereby being shifted from the straight lines. From this shift amount, it is possible to reproduce the phase change amount via image processing such as, e.g., Fourier transformation method.

In JP-A-2002-117800, as an application embodiment of the off-axis electron beam holography method, an interference electron microscope using an electron beam biprism is disclosed. In the interference electron microscope described in JP-A-2002-117800, optical path of the electron beam is divided using the apparatus called the biprism, thereby generating an interference fringe on the transmission electron image. The unit used as the electron beam biprism is a one which is equipped with electrically-conductive property by applying metal evaporation on the surface of a glass fiber which is 300 nm to 600 nm in diameter and about a few mm long. Although no concrete disclosure is made in JP-A-2002-117800, phase information on the electromagnetic field of the sample is calculated based on the interference fringe generated.

In J. Cumings, A. Zettl, and M. R. McCarthy; "Carbon Nanotube Electrostatic Biprism: Principle of Operation and Proof of Concept". Microsc. Microanal. 10 (2004) 420424, in a process where the observation is made using a transmission electron microscope in a state where electric potential is applied to carbon nanotubes, a possibility is studied that the carbon nanotubes can be used as the electron beam biprism of the off-axis electron beam holography method, and experiments associated therewith are made.

Meanwhile, as a methodology for making the observation of a phase object in a simplified manner, the Lorentz electron microscope method (defocus method) has been in use from olden times. In the Lorentz electron microscope method, however, there have existed two problems, i.e., low resolution and lack of quantitative property. In recent years, this defocus method has been improved. As a result, the TIE (: Transport of Intensity Equation) method, i.e., a methodology for visualizing the phase quantitatively, is disclosed in. e.g., Teague, M. R.; "Deterministic Phase Retrieval: A Green's Function Solution". J. Opt. Soc. Am. 73 (1983) 1434 to 1441. Attention is now focused on this TIE method as an alternative method for the interference electron microscope method. This methodology is applicable to optical microscopes, X-ray microscopes, and electron microscopes.

Also, in V. V. Volkov and Y. Zhu; "Lorentz phase microscopy of magnetic materials". Ultramicroscopy 98 (2004) 271 to 281, a proposal is made concerning the MTIE (: Magnetic Transport of Intensity Equation) method which results from applying the above-described TIE method to magnetic materials. Then, this MTIE method is applied to the visualizing of in-plane components of lines of magnetic force within a magnetic thin film. In this way, from the viewpoint of the quantitative property, the alternative methods such as the TIE method are not comparable to the interference electron microscope method. It is expected from the viewpoint of simplicity and wideness of observation area, however, that these alternative methods will be used from now on in a complementary manner with the interference electron microscope method.

SUMMARY OF THE INVENTION

According to the TIE method or the MTIE method, it is possible to analyze the electromagnetic-field vectors of a sample quantitatively. It is theoretically required, however, that the image of one and the same field-of-view be acquired under three conditions of over focus, under focus, and in focus. Accordingly, there exists a drawback that it takes a time to acquire the three pieces of images. Also, there exists a problem that it is difficult to achieve the exact position alignment among the three pieces of images when trying to acquire them. In the case of an optical microscope, changing position of the objective lens allows implementation of the adjustment of the focus. Consequently, magnification changes, rotations, and displacements of the images caused by the objective-lens adjustment do not result in a very serious problem. In the case of an electron microscope, however, the adjustment of the focus is made by the adjustment of current value of the objective lens. This feature changes the magnifications of the respective over-focus, under-focus, and in-focus images, and also gives rise to relative rotations and distortions of the images. If the position alignment among the images is inappropriate, reliability and measurement accuracy will be lowered in the result acquired. Conversely speaking, enhancing the measurement accuracy requires that the position alignment among the images be precisely achieved at the expense of the observation throughput. Moreover, the amount acquired by the MTIE method is the phase change amount. However, deriving the magnetic-field component vector of the sample requires that the differential calculation for the phase change amount be executed. As a result, there exists a possibility that the accuracy may be lowered in comparison with a method of directly measuring the spatial differentiation amount of the phase change.

Meanwhile, the currently-existing interference electron microscope necessitates installments of an electron gun exhibiting high coherence, the electron beam biprism, an image acquisition apparatus, and an analysis apparatus. This situation results in a problem that the cost of the apparatuses becomes extremely high. Also, from the apparatus configuration, the vacuum area through which the reference wave passes through is required in the vicinity of an observation field-of-view. As a result, the wideness of an area which is observable at one time is determined by the wideness of the interference area of the electron beams. In the currently-existing electron beam technologies, however, the wideness of the interference area of the electron beams is limited to an order of about a few microns. Accordingly, in the currently-existing interference electron microscope, it is difficult to observe a wide area with a high spatial resolution. If the area of the interference fringe is forcefully enlarged with the spatial resolution kept constant, the contrast of the interference fringe is lowered. This results in the occurrence of a drawback that the high-accuracy measurement becomes impossible. Consequently, when observing a wide area while maintaining a constant spatial resolution, it turns out that observing a narrow area will be repeated in a two-dimensional manner. This situation necessitates an exceedingly-long observation time, which is not realistic.

The present invention has been devised in order to solve these problems. Accordingly, an object of the present invention is to provide an electron-microscope application apparatus whose structure is simplified as compared with the conventional technologies, and which allows the electromagnetic-field structure of a sample (in particular, the magnetic-domain structure or magnetic-field distribution within a magnetic thin film) to be quantitatively observed at a higher speed as compared with the conventional technologies.

In the present invention, the following method makes it possible to quantitatively visualize the phase change in an electron beam due to the magnetic-field structure of a sample: Namely, an extremely narrow electrically-conductive fiber is used instead of the 300-nm to 600-nm-diameter electron beam biprism used in the conventional interference electron microscope method. Although the diameter of the electrically-conductive fiber is an amount determined depending on resolution of the phase change amount, typically, an about-5-nm to 50-nm-diameter electrically-conductive fiber is used for example. Moreover, a phenomenon is utilized where a focus-shifted shadow of this electrically-conductive fiber or an emission line is shifted from a straight line. Here, this emission line is generated by a phenomenon that applying a feeble electric potential to the electrically-conductive fiber will superpose the electron beam on the center of the electrically-conductive fiber. This shift amount of the shadow of the electrically-conductive fiber or the one of the emission line is proportional to a differentiation of the phase change amount of the electron beam due to the magnetic-field structure of the sample with respect to a direction perpendicular to the electrically-conductive fiber. Accordingly, the phase change amount can be quantified by calibrating this shift amount through its comparison with a shift amount caused by another sample in terms of which the corresponding phase change amount has been already known in advance. Furthermore, if necessary, it is possible to quantitatively transform the differentiation of the phase change amount back to the phase change amount by integrating this differentiation. Here, a one-dimensional distribution resulting from measuring the shift amount of the shadow of the electrically-conductive fiber or the one of the emission line along the electrically-conductive fiber is a one-dimensional distribution of the differentiation of the phase change amount of the electron beam with respect to the direction perpendicular to the electrically-conductive fiber at a sample position on which the shadow of the electrically-conductive fiber is superposed. Scanning the sample in the direction perpendicular to the electrically-conductive fiber makes it possible to acquire a two-dimensional distribution of the differentiation amount of the phase change. In addition, in order to measure a differentiation with respect to a direction along the electrically-conductive fiber, the sample is scanned in the direction perpendicular to the above-described scanning direction, then performing the measurement similarly. Here, the magnetic-field component vector of the sample is calculated based on the acquired two-dimensional distribution, thereby being visualized.

According to the present invention, it becomes possible to acquire the electromagnetic-field structure of a sample, and in particular, the magnetic-domain structure image of the sample at a low cost. Also, it becomes possible to precisely measure the two-dimensional magnetic-field component distribution within the sample surface. This is because the magnetic-field component within the sample surface is directly proportional to the differentiation amount of the phase change amount with respect to the direction perpendicular to the magnetic-field component. Also, since the vacuum area is unnecessary which is necessary in the conventional interference electron microscope method, there exists no limit to the wideness of an observation area. This feature makes it possible to observe a wide area as long as time and throughput permit it.

Other objects, features and advantages of the invention will become apparent from the following description of the embodiments of the invention taken in conjunction with the accompanying drawings.

DESCRIPTION OF THE INVENTION

Embodiment 1

Figure 1:
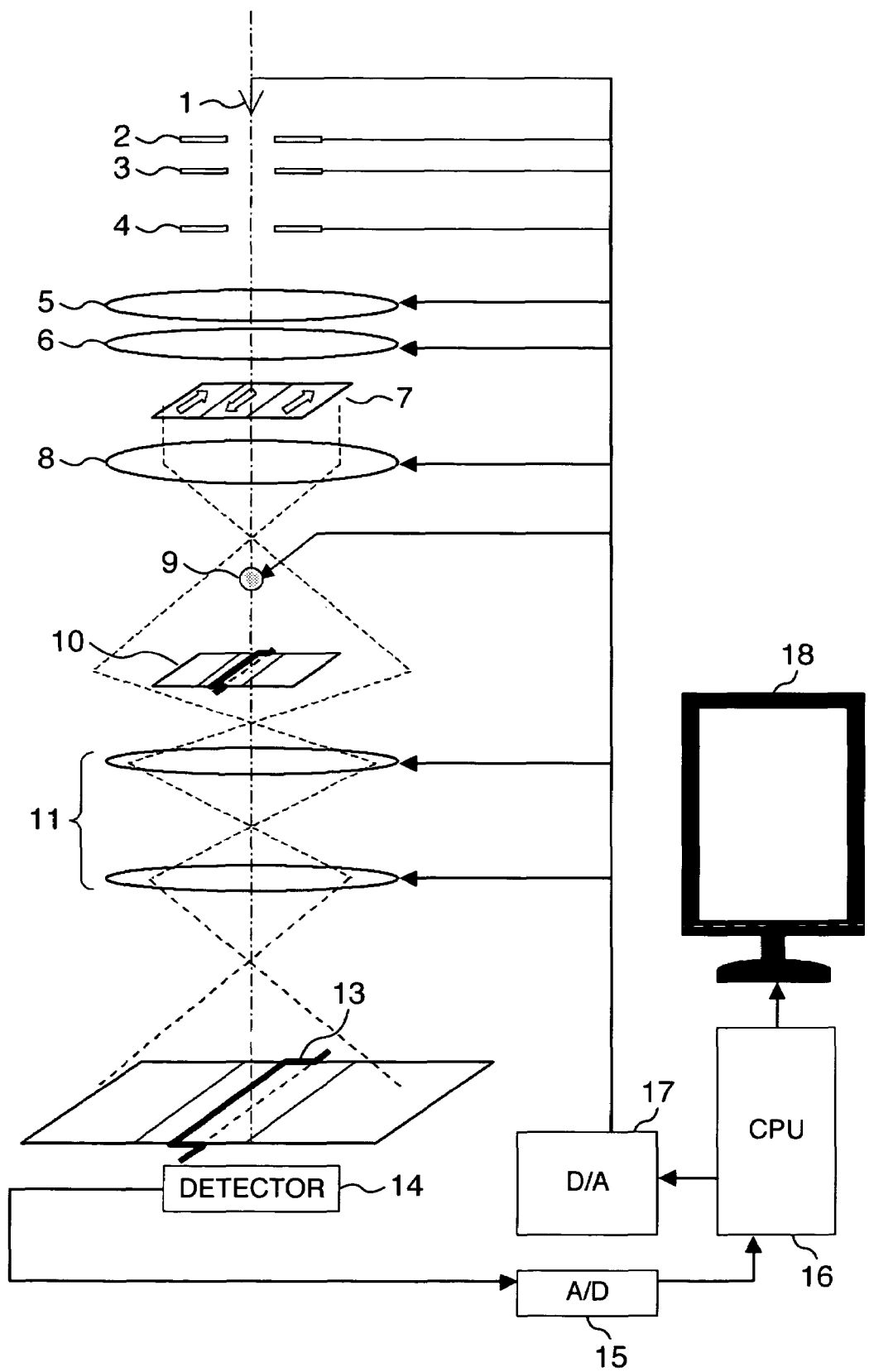
FIG. 1 is a diagram for explaining a carry-out method in a first embodiment.
Figure 2:
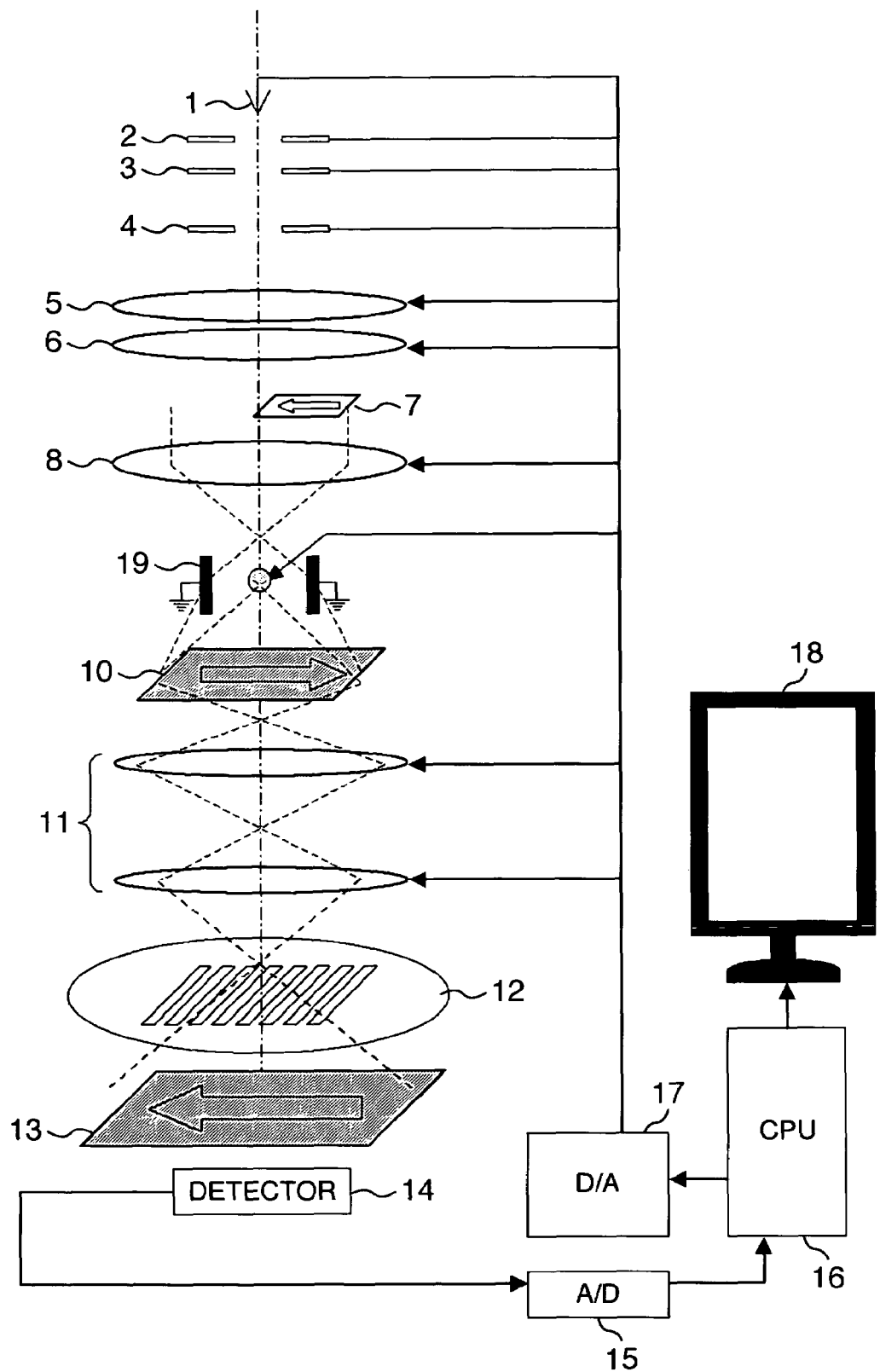
FIG. 2 is the diagram for explaining the off-axis electron beam holography method.

Hereinafter, referring to FIG. 1, the explanation will be given below concerning an example of the apparatus used in the present first embodiment.

The apparatus used in the present first embodiment basically includes components such as an irradiation optical system, an image-forming optical system, a sample stage, and a control system. The irradiation optical system includes components such as an electron source 1, a first extraction electrode 2, a second extraction electrode 3, an acceleration electrode 4, a first condenser lens 5, and a second condenser lens 6. An electron beam, which is extracted from the electron source 1 by applying a voltage to the first extraction electrode 2 and the second extraction electrode 3, is accelerated up to a predetermined velocity by the acceleration electrode 4. Moreover, a sample 7 is irradiated under an appropriate irradiation condition by using such components as the first condenser lens 5 and the second condenser lens 6. The image-forming optical system includes components such as an objective lens 8, an image-forming lens system 11, an electrically-conductive fiber 9, and a two-dimensional detector 14. The electrically-conductive fiber 9 set up between the objective lens 8 and the image-forming lens system 11 is grounded. The control system includes components such as a CPU 16, a D/A converter 17, and an A/D converter 15. Also, on an image surface 10 of the objective lens 8, a shadow of the electrically-conductive fiber 9 occurs over an image of the sample 7. A magnified image 13 of this shadow is formed by the image-forming lens system 11, then being inputted into the two-dimensional detector 14. An input image from the detector 14 is introduced into the CPU (i.e., arithmetic-operation unit) 16 via the A/D converter 15. Also, operation conditions on the components, such as the electron source 1, the first extraction electrode 2, the second extraction electrode 3, the acceleration electrode 4, the first condenser lens 5, the second condenser lens 6, the objective lens 8, the electrically-conductive fiber 9, and the image-forming lens system 11, are controlled from the CPU 16 via the D/A converter 17.

This image input is sequentially performed while scanning the sample 7, thereby being transformed into a shift amount of the shadow of the electrically-conductive fiber 9 due to the sample 7. The image of the interference fringe inputted from the detector 14 is introduced into the CPU 16 via the A/D converter 15, then being subjected to the two-dimensional Fourier transformation processing. Inside the Fourier space, amplitude change and phase change in the sample which are superposed on the interference fringe are included in such a manner that a peak called "sideband" is positioned at their center. By extracting the amplitude change and phase change and applying the inverse two-dimensional Fourier transformation thereto, it becomes possible to reproduce the amplitude change and phase change due to the sample. The amplitude change and phase change reproduced are displayed on a display apparatus 18.

Figure 8:
FIG. 8 is a diagram for explaining the wideness of a shadow which occurs by the conventional 500-nm-diameter electron beam biprism.

Here, the narrower the shadow of the electrically-conductive fiber 9 becomes, the more capable it becomes to perform the higher spatial-resolution measurement. In the so-called electron beam biprism, however, the shadow cannot be made narrow enough. Here, the so-called electron beam biprism is used in the conventional interference electron microscope method, and is fabricated by evaporating a metal on an about-300-nm to 600-nm-diameter glass fiber. As an example, FIG. 8 illustrates a drawing where about-100-nm-diameter latex particles are observed in a state where an about-a-few-V electric potential is applied to the conventional electron beam biprism. This drawing shows that, under the present condition, the shadow is thick, i.e., an order of the one-a-few-tenths as compared with the diameter of the particles. Accordingly, it is impossible to measure a fine curvature. Nevertheless, by employing the 50-nm-or-less-diameter electrically-conductive fiber used in the present embodiment, it becomes possible to make the shadow equal to the one-tenth or less as compared with the conventional electron beam biprism. This makes it possible to perform the observation with the high spatial resolution.

It is conceivable that a carbon nanotube or a metal whisker is usable as the electrically-conductive fiber used in the present embodiment. Some other material, however, is also usable as long as it has such characteristics as suitable diameter, electrically-conductive quality, stability, and strength.

Also, the high-coherence electron beam is necessary in the conventional interference electron microscope method. In contrast thereto, the coherence is unnecessary in the method of the present embodiment. On account of this, the same apparatus specification as that of the conventional electron microscopes is quite preferable. This feature allows a tremendous lowering in the apparatus cost.

Figure 3A:
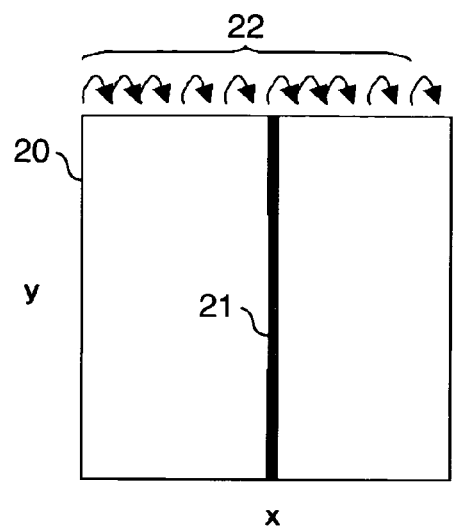
FIG. 3A to FIG. 3D are diagrams for explaining the measurement principle in the first embodiment, in particular, an algorithm for quantifying the shift in the shadow of the electrically-conductive fiber.
Figure 3B:
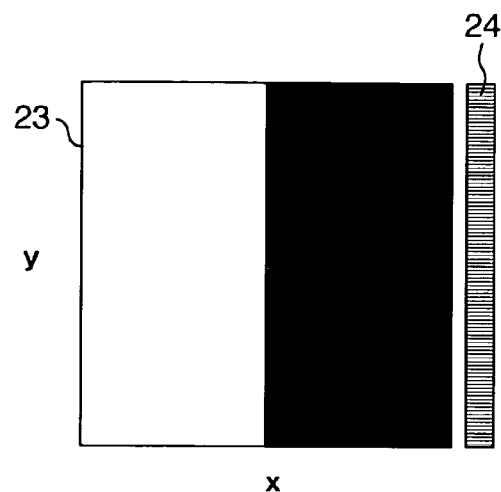
Figure 3C:
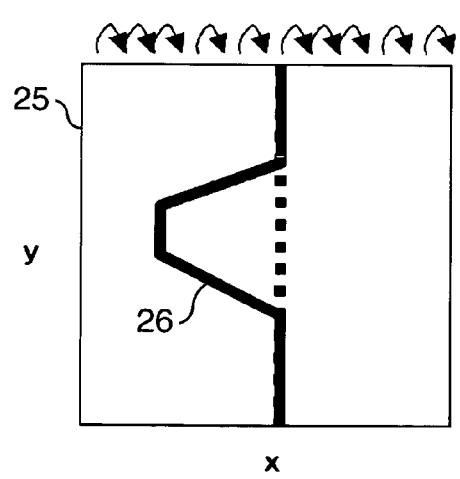
Figure 3D:
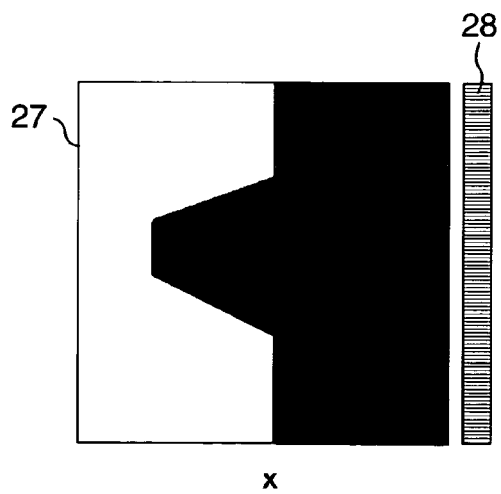
Figure 4:
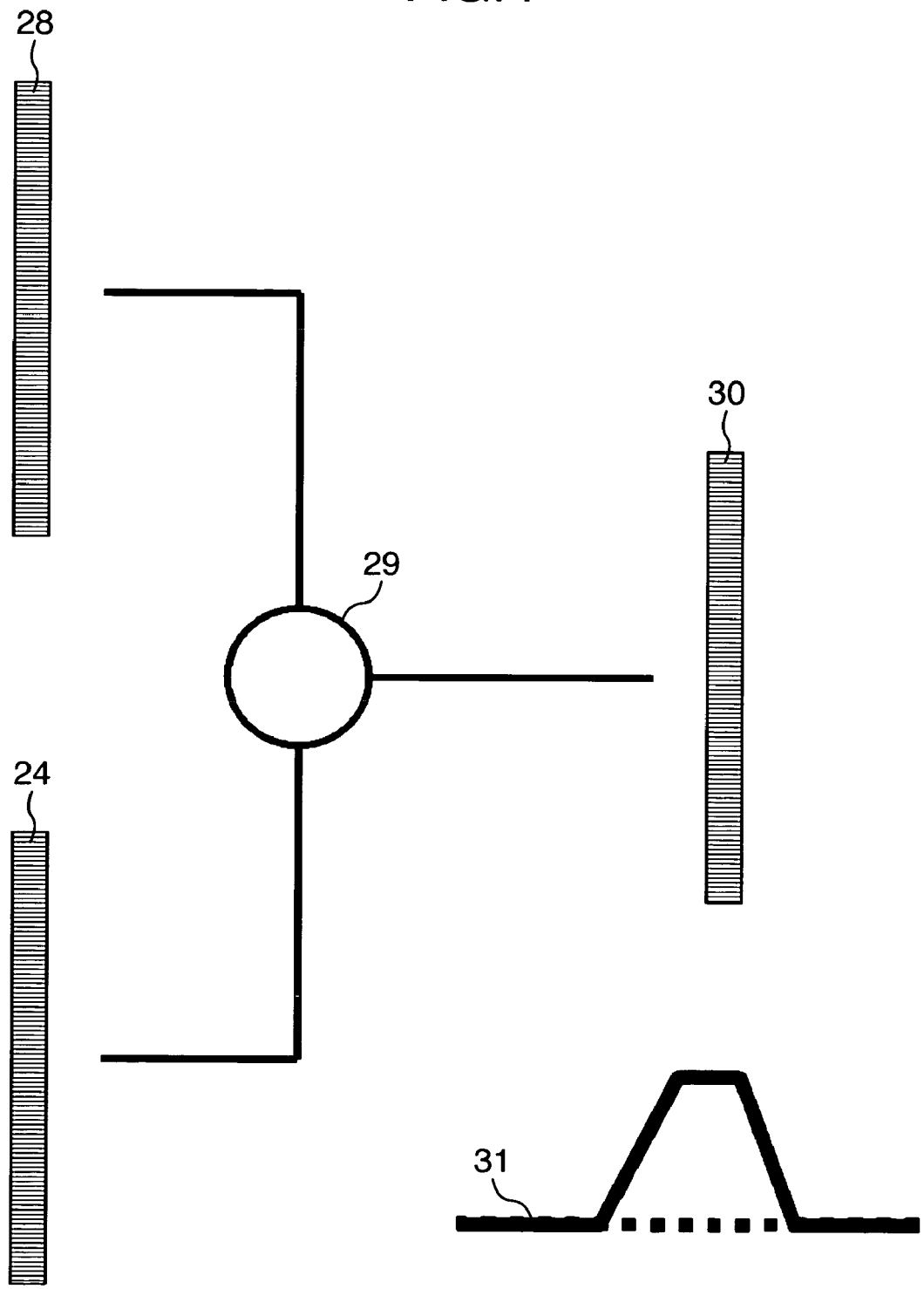
FIG. 4 is a diagram for explaining the measurement principle in the first embodiment, in particular, the algorithm for quantifying the shift in the shadow of the electrically-conductive fiber.

Next, referring to FIG. 3A to FIG. 3D and FIG. 4, the explanation will be given below concerning an algorithm for quantifying the shift amount of the shadow of the electrically-conductive fiber 9 inside the arithmetic-operation unit 16. In the following explanation, it is assumed that all of the arithmetic operations are executed by the CPU 16. First, the shadow of the electrically-conductive fiber in a state where there exists no sample is inputted as a two-dimensional image. Here, for simplicity of the explanation, it is assumed that the shadow exists along the y direction, and that the direction perpendicular to the shadow is defined as the x direction. In the case where there exists no sample as is illustrated in FIG. 3A, the shadow becomes a line 21 in the y direction. With respect to the image of the inputted shadow, a successive integration 22 of the value of each pixel continues to be executed in the x direction from the end (left-side end or right-side end; the explanation from the left-side end is given in FIG. 3A) of the image. Definition of this successive integration 22 is a manipulation that the value acquired by adding the value of a left-side pixel to the value of a right-side pixel adjacent thereto is newly defined as the value of the right-side pixel. With respect to all the pixels in the y direction, the present manipulation is performed from the left-side end to the right-side end of the image in the x direction. Then, a newly image which turns out to be acquired after the completion of the present manipulation is an image 23 as is illustrated in FIG. 3B. Moreover, with respect to the image 23 illustrated in FIG. 3B, an integration of the value of each pixel in the y direction is executed in the x direction. A one-dimensional image in the y direction which turns out to be acquired as a result of the present manipulation is an image 24. The image 24 has an amount proportional to a distance of the center of the shadow from the right-side end of the image in each pixel in the y direction. The one-dimensional image 24, which has the distance of the center of the shadow from the right-side end of the image in each pixel in the y direction, is acquired in advance in the state where there exists no sample, then being stored into an appropriate storage apparatus beforehand. Next, in a state where there exists the sample, the shadow 26 of the electrically-conductive fiber is inputted (FIG. 3C). A manipulation of the same successive integration and integration as the ones executed in the state where there exists no sample is executed, thereby acquiring a new one-dimensional image 28 (FIG. 3D). The value of each pixel of the one-dimensional image 24 in the y direction in the state where there exists no sample is subtracted from the value of each pixel of the new one-dimensional image 28 in the y direction in the state where there exists the sample (FIG. 4). This manipulation 29 quantifies the shift amount of the shadow of the electrically-conductive fiber in the x direction, i.e., in the direction perpendicular to the electrically-conductive fiber, in the state where there exists the sample. Also, quantifying the shift may be sequentially executed every time the image is acquired. Otherwise, quantifying the shift may also be performed by storing the image information into an image memory or the like beforehand, and executing the image arithmetic operation for the accumulated images.

The execution of the above-described processing steps makes it possible to acquire the two-dimensional data on the differentiation amount of the phase change of the electron beam due to the sample with respect to the direction perpendicular to the electrically-conductive fiber. Next, the two-dimensional data on the differentiation amount of the phase change of the electron beam due to the sample with respect to the direction parallel to the electrically-conductive fiber is acquired, using either of the following two methods: Namely, (1) a method of rotating the electrically-conductive fiber by 90° within a plane perpendicular to the electron beam, and scanning the sample in a direction perpendicular to the electrically-conductive fiber rotated, and (2) a method of adding no change to the direction of the electrically-conductive fiber, and scanning the sample in a direction perpendicular to the electrically-conductive fiber in a state where the sample is rotated by 90° within the plane perpendicular to the electron beam.

In the case of the method (1), since the direction of the detector must also be rotated by 90° within the plane, it takes a time to make the adjustment. Accordingly, one or more sets of the electrically-conductive fibers which have the same diameter and are perpendicular to each other within the plane, and further, one or more sets of the detectors which are perpendicular to each other within the plane, are prepared in advance inside the electron microscope. This preparation makes it possible to make the measurement swiftly.

In the case of the method (2), it is effective enough to control the deflector by the arithmetic-operation unit 16. Consequently, the direction of the detector need not be rotated, and thus it is unnecessary to make the adjustment. The execution of either of the method (1) and the method (2) allows the acquisition of the two-dimensional data on the differentiation amount of the phase change of the electron beam due to the sample with respect to the directions which are perpendicular to each other within the sample surface.

Figure 5A:
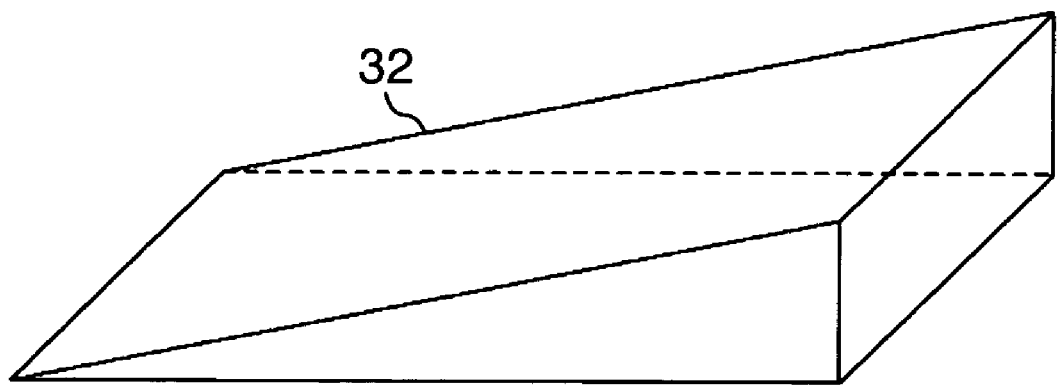
FIG. 5A and FIG. 5B are diagrams for explaining the measurement principle in the first embodiment, in particular, an algorithm for transforming the quantified shift in the shadow of the electrically-conductive fiber into the differentiation amount of the phase.
Figure 5B:
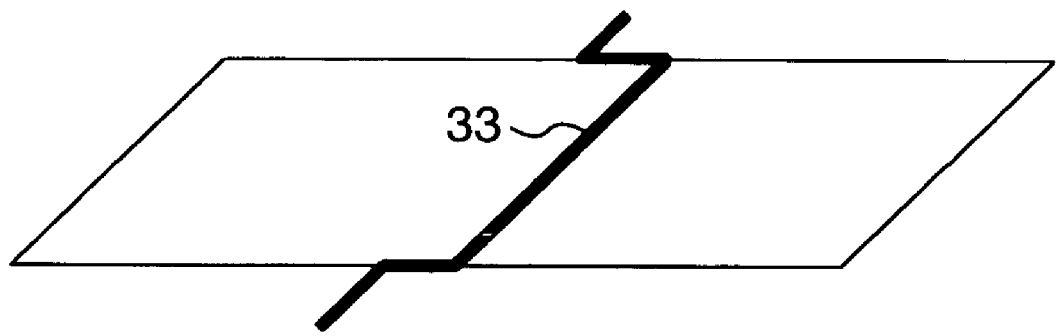

Next, referring to FIG. 5A and FIG. 5B, the explanation will be given below concerning a method for transforming the shift amount of the shadow quantified as described above into an absolute value by calibrating this shift amount through the comparison with another sample in terms of which the corresponding phase change amount has been already known in advance. First, a sample is prepared for which the corresponding phase is changed in a one-dimensional direction with a constant ratio. The sample which can be mentioned as the one like this is, e.g., a uniform-density wedge-shaped thin film 32 as is illustrated in FIG. 5A. It is recommendable to prepare beforehand a standard sample in terms of which the corresponding phase change amount has been measured in advance by the interference electron microscope method or the like. A shift 33 in the shadow due to this standard sample (FIG. 5B) is quantified using the algorithm explained earlier, thereby determining a proportion coefficient with the already-known phase change ratio for the sample. It is preferable to carry out beforehand the determination of this proportion coefficient before the actual observation of the sample. Also, this proportion coefficient is stored into a register inside the CPU 16 in FIG. 1, or is stored into (although not illustrated in FIG. 1) a storage apparatus which accompanies the CPU 16.

Now, a two-dimensional image is acquired by quantifying the shift amount of the shadow, and transforming the quantified shift amount into the absolute phase change amount by multiplying the quantified shift amount by the proportion coefficient determined in advance. This two-dimensional image is the two-dimensional distribution of the differentiation of the phase change with respect to the scanning direction of the sample carried out above. Moreover, by performing a similar scanning by rotating the relative position relationship between the sample and the electrically-conductive fiber by 90°, it becomes possible to acquire a two-dimensional distribution of the two-dimensional differentiation of the phase change. As the method for rotating this relative position relationship by 90°, there exist the following two methods: Namely, (1) a method of rotating the sample by 90°, and performing the successive integration and the integration of the image in the x direction while scanning the sample in the x direction, and (2) a method of rotating the electrically-conductive fiber by 90°, and performing the successive integration and the integration of the image in the y direction while scanning the sample in the y direction. Either of these two methods is recommendable.

Hereinbefore, the explanation has been given concerning the processing steps which make it possible to acquire the two-dimensional distribution of the two-dimensional differentiation amount of the phase change of the electron beam due to the sample. Next, the explanation will be given below concerning a method for acquiring the magnetic vector within the sample surface from the two-dimensional distribution of the differentiation amount of the phase change of the electron beam due to the sample (which has been acquired here). If the effect of the electric field is negligible, the following relationship exists between the two-dimensional distribution of the differentiation amount of the phase change and the magnetic vector within the sample surface:

$$\begin{cases} B_x = \frac{1}{t} \cdot \frac{h}{2\pi e} \cdot \frac{\partial \varphi(x,y)}{\partial y} \\ B_y = -\frac{1}{t} \cdot \frac{h}{2\pi e} \cdot \frac{\partial \varphi(x,y)}{\partial x} \end{cases} \quad \text{Expression (1)}$$

Here, t denotes thickness of the thin film, h denotes Planck constant ($\approx 6.626 \times 10^{-34}$), and e denotes electron's elementary electric charge ($\approx 1.59 \times 10^{-19}$). Also, $B_x$, $B_y$ respectively denote the x-direction component and y-direction component of the magnetic vector within the sample surface, and $\partial\phi(x, y)/\partial x$ and $\partial\phi(x, y)/\partial y$ respectively denote the x-direction component and y-direction component of the two-dimensional distribution of the differentiation amount of the phase change. Consequently, the use of the Expression (1) makes it possible to transform the two-dimensional distribution of the differentiation amount of the phase change (acquired in the present embodiment) into the magnetic-vector components within the sample surface.

Furthermore, by applying an integration operation to the differentiation amount of the phase change, it is possible to transform the differentiation amount of the phase change into the phase itself. This is particularly useful in the case where the sample is not the magnetic substance but contains an electric field. In the present embodiment, the sample is assumed as the magnetic sample. It is needless to say, however, that the present invention is applicable to all of samples which cause the phase change of the electron beam to occur by the electromagnetic field. For example, in the case of a dielectric sample, the differentiation amount of the phase change in the x direction is proportional to the x-direction component of the polarization vector, and the differentiation amount of the phase change in the y direction is proportional to the y-direction component of the polarization vector. Taking advantage of this fact makes it possible to visualize the in-plane component of the polarization vector of the dielectric sample.

Incidentally, a feature of the electrically-conductive fiber used in the present embodiment is that electrically-conductive fibers having different diameters are made selectable depending on the wideness of an observation target. For example, four types of electrically-conductive fibers whose diameters are equal to 50 nm, 25 nm, 10 nm, and 5 nm are mounted beforehand on a holder having a movable mechanism in vacuum. This mounting permits the observer to select whatever of them depending on the wideness (i.e., magnification) of the observation target. This is performed in order to avoid the following situation: Namely, if an unnecessarily small shadow is used for a large observation target, it takes an exceedingly-long time to acquire the data, thereby lowering the observation throughput tremendously. Of course, it is needless to say that, if a wide area is wished to be observed with a high spatial resolution even if the observation throughput is lowered, it is advisable to select an electrically-conductive fiber having a smaller diameter.

In the present embodiment, the explanation has been given concerning the example where the electrically-conductive fiber is located at the same position as that of the electron beam biprism used in the interference electron microscope method. The position at which the electrically-conductive fiber is to be located may be anywhere unless it is not a position at which the focus is achieved with the sample in an electro-optics manner. Moreover, the electrically-conductive fiber may also be located in the irradiation system so as to project the real shadow of the electrically-conductive fiber onto the sample.

Embodiment 2

FIG. 6A to FIG. 6D illustrate one mode of another embodiment. The present embodiment is an embodiment where the electron microscope illustrated in FIG. 1 is applied to observation of the magnetic-domain structure of a magnetic thin film.

Figure 6A:
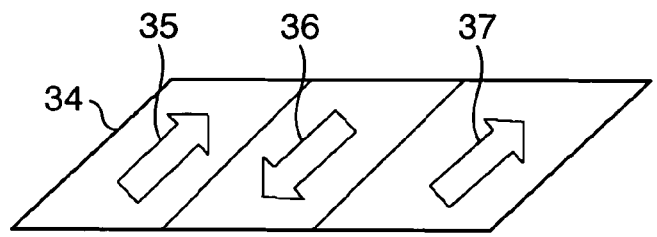
FIG. 6A to FIG. 6D are diagrams for explaining a second embodiment.
Figure 6B:
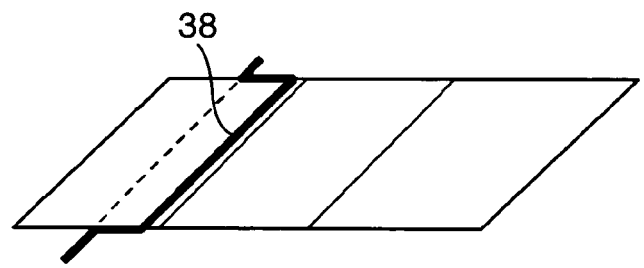
Figure 6C:
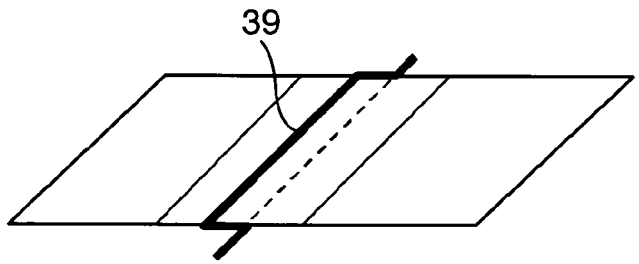
Figure 6D:
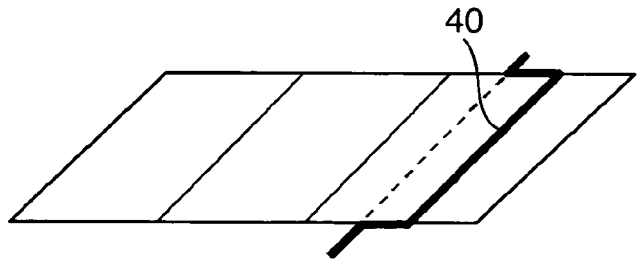

The sample in the present embodiment is a magnetic thin film 34. Here, it is assumed that the magnetic thin film 34 includes therein three different magnetic-domain structures 35, 36, and 37 (FIG. 6A). Let's consider a case where, with respect to the shadow of the electrically-conductive fiber in the present embodiment, the magnetic thin film 34 is scanned from the right to the left in the drawing (the shadow of the electrically-conductive fiber is displaced from the left to the right in the drawing). At this time, in the magnetic-domain structure 35, the shadow of the electrically-conductive fiber is shifted as is implemented by a shadow 38 (FIG. 6B). This shift in the shadow, which has occurred in the direction perpendicular to the electrically-conductive fiber, indicates the existence of a magnetic-vector component in the direction parallel to the electrically-conductive fiber as was shown by the Expression (1). Then, while scanning the sample, this shift amount of the shadow is quantified using the algorithm explained in the first embodiment. Next, in the magnetic-domain structure 36, the shadow of the electrically-conductive fiber is shifted as is implemented by a shadow 39 (FIG. 6C). The fact that the direction of this shift is the opposite to the direction of the shift in the magnetic-domain structure 35 indicates that the direction of the magnetic vector in the magnetic-domain structure 36 is the opposite to the direction of the magnetic vector in the magnetic-domain structure 35. Furthermore, the scanning is continued, and in accompaniment therewith, in the magnetic-domain structure 37, the shadow of the electrically-conductive fiber is shifted as is implemented by a shadow 40 (FIG. 6D). Termination of the sample scanning in this way allows acquisition of data on the magnetic-vector component in the direction parallel to the electrically-conductive fiber. Here, rotating the sample or rotating the electrically-conductive fiber makes it possible to acquire data on a magnetic-vector component in the direction perpendicular thereto. Displaying these pieces of data on the magnetic-vector components makes it possible to visualize the magnetic-domain structures 35, 36, and 37 illustrated in FIG. 6A. These pieces of data are stored into the register inside the CPU 16 in FIG. 1, or are stored into (although not illustrated in FIG. 1) an external memory which accompanies the CPU 16.

As explained above, according to the present embodiment, it becomes possible to visualize the microscopic magnetic-domain structures of magnetic thin films. The implementation of this visualization plays a significant role of enhancing characteristics of devices using these materials, e.g., a magnetic head used in hard disc, or characteristics of magnetic storage media using these materials, e.g., a hard-disc medium.

Embodiment 3

FIG. 7A to FIG. 7D schematically illustrate another mode of the present embodiment. The present embodiment is an embodiment where the electron microscope illustrated in FIG. 1 is applied to observations of the magnetic-domain structure of a magnetic fine particle and a leakage magnetic field.

Figure 7A:
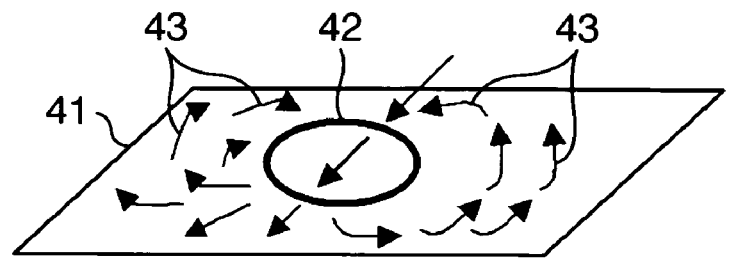
FIG. 7A to FIG. 7D are diagrams for explaining a third embodiment.
Figure 7B:
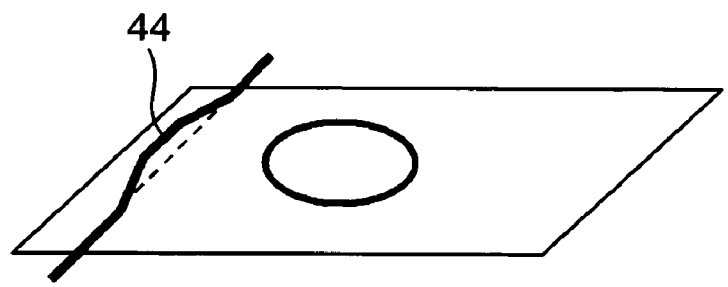

The sample in the present embodiment is a magnetic fine particle 42 supported by a magnetic thin film 41, and a leakage magnetic field 43 exist on the periphery of the particle 42 (FIG. 7A). Let's consider a case where, with respect to the shadow of the electrically-conductive fiber in the present embodiment, the magnetic thin film 41 is scanned from the right to the left in the drawing by displacing the sample stage (the shadow of the electrically-conductive fiber is displaced from the left to the right in the drawing). At this time, the shadow of the electrically-conductive fiber is shifted as is implemented by a shadow 44 (FIG. 7B).

Figure 7C:
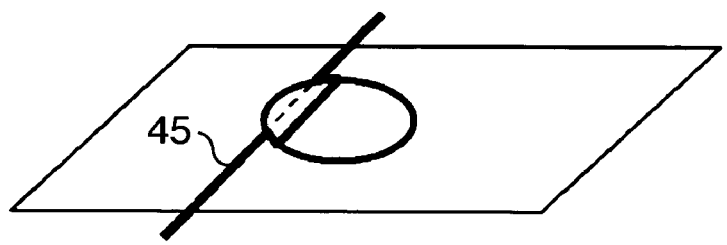
Figure 7D:
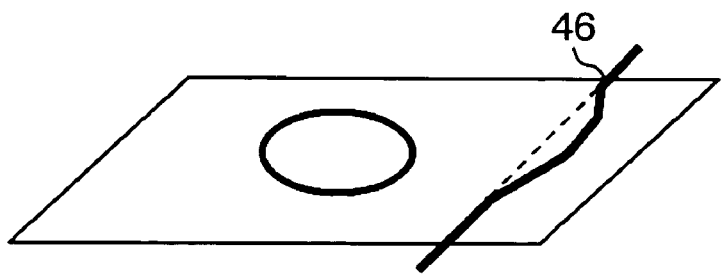

Then, while scanning the sample stage, this shift amount of the shadow is quantified using the algorithm explained in the first embodiment. Next, the shadow of the electrically-conductive fiber is shifted as is implemented by a shadow 45 (FIG. 7C). Furthermore, the scanning is continued, and in accompaniment therewith, the shadow of the electrically-conductive fiber is shifted as is implemented by a shadow 46 (FIG. 7D). Termination of the sample scanning in this way allows acquisition of data on a magnetic-vector component in the direction parallel to the electrically-conductive fiber. Here, rotating the sample or rotating the electrically-conductive fiber makes it possible to acquire data on a magnetic-vector component in the direction perpendicular thereto. Displaying these pieces of data on the magnetic-vector components makes it possible to visualize the magnetic-field distribution illustrated in FIG. 7A. These pieces of data are stored into the register inside the CPU 16 in FIG. 1, or are stored into (although not illustrated in FIG. 1) the storage apparatus which accompanies the CPU 16. As explained above, according to the present embodiment, it becomes possible to visualize the microscopic magnetic-domain structures of magnetic fine particles. The implementation of this visualization plays a significant role of enhancing characteristics of magnetic storage media using these materials, e.g., a large-capacity magnetic tape.

The present embodiment relates to the electron microscope used for evaluating the magnetic characteristics of a microscopic area.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An electron microscope, comprising:
a sample stage for mounting a sample thereon,
an irradiation optical system for irradiating said sample with an electron beam,
an electron-beam detector for detecting said electron beam which has passed through said sample,
an electrically-conductive fiber located at a position through which said electron beam will pass between said sample stage and said electron-beam detector, said electron beam having passed through said sample,
means for applying an electric voltage to said electrically-conductive fiber, and
an arithmetic-operation apparatus for measuring amount of a distortion from a detection signal of said electron-beam detector, and calculating an electric-field or magnetic-field vector in said sample from said distortion amount, said distortion occurring in a shadow of said electrically-conductive fiber projected onto a transmission image of said sample.

2. The electron microscope according to claim 1, wherein said electrically-conductive fiber is a carbon nanotube or metal whisker which is 50 nm or less in diameter.

3. The electron microscope according to claim 1, wherein electrically-conductive fibers having different diameters are selectable depending on size of said sample or wideness of an observation area.

4. The electron microscope according to claim 1, wherein there are provided one or more sets of electrically-conductive fibers which are perpendicular to each other within a plane.

5. The electron microscope according to claim 1, wherein an accumulative integration of an image of said shadow of said electrically-conductive fiber is sequentially executed in a direction perpendicular to said electrically-conductive fiber, and
a subtraction between an accumulative-integration value acquired by said accumulative integration and an accumulative-integration value of said electrically-conductive fiber acquired in a state where there exists no sample is defined as said shift amount of said shadow of said electrically-conductive fiber.

6. The electron microscope according to claim 1, wherein said shift amount of said shadow of said electrically-conductive fiber is calibrated in advance by using a sample in terms of which a phase change amount has been already known.

* * * * *